(12) United States Patent
Ikegami et al.

(10) Patent No.: US 9,095,604 B2
(45) Date of Patent: Aug. 4, 2015

(54) COMPOSITION FOR PREVENTING INFLAMMATIONS

(75) Inventors: Shuji Ikegami, Odawara (JP); Seiya Makino, Odawara (JP); Takayuki Toshimitsu, Odawara (JP); Hiroyuki Itoh, Odawara (JP); Atsuhito Nakao, Kofu (JP)

(73) Assignee: Meiji Co, Ltd., Tokyo (JP)

( * ) Notice: Subject to any disclaimer, the term of this patent is extended or adjusted under 35 U.S.C. 154(b) by 0 days.

(21) Appl. No.: 13/821,284

(22) PCT Filed: Sep. 8, 2011

(86) PCT No.: PCT/JP2011/070436
§ 371 (c)(1),
(2), (4) Date: Jun. 5, 2013

(87) PCT Pub. No.: WO2012/033151
PCT Pub. Date: Mar. 15, 2012

(65) Prior Publication Data
US 2013/0302844 A1    Nov. 14, 2013

(30) Foreign Application Priority Data
Sep. 9, 2010   (JP) .................................. 2010-202383

(51) Int. Cl.
| A61K 35/747 | (2015.01) |
| A23L 1/30 | (2006.01) |
| A61K 35/741 | (2015.01) |
| C12N 1/20 | (2006.01) |
| C12R 1/225 | (2006.01) |
| A23K 1/00 | (2006.01) |
| A61K 31/192 | (2006.01) |
| A61K 35/745 | (2015.01) |
| A23C 9/123 | (2006.01) |
| C12Q 1/02 | (2006.01) |
| C12Q 1/68 | (2006.01) |

(52) U.S. Cl.
CPC ............. *A61K 35/747* (2013.01); *A23C 9/1238* (2013.01); *A23K 1/009* (2013.01); *A23L 1/3014* (2013.01); *A61K 31/192* (2013.01); *A61K 35/741* (2013.01); *A61K 35/745* (2013.01); *C12N 1/20* (2013.01); *C12Q 1/02* (2013.01); *C12Q 1/6897* (2013.01); *C12R 1/225* (2013.01); *A23V 2200/3204* (2013.01); *A23Y 2220/15* (2013.01); *A23Y 2220/29* (2013.01); *A23Y 2240/75* (2013.01); *G01N 2500/10* (2013.01); *G01N 2800/06* (2013.01)

(58) Field of Classification Search
None
See application file for complete search history.

(56) References Cited

U.S. PATENT DOCUMENTS
2007/0298019 A1 * 12/2007 Bojrab ...................... 424/93.45
2008/0050766 A1   2/2008 Kitamura et al.

FOREIGN PATENT DOCUMENTS
EP       1 767 622 A1    3/2007
WO   WO 2005/113767 A1  12/2005

OTHER PUBLICATIONS

Gambone, C.J. et al. 2002. Unique Property of Some Synthetic Retinoids: Activation of the Aryl Hydrocarbon Receptor Pathway. Molecular Pharmacology 61/2: 334-342; specif. 334-335, 337.*
Ulcerative Colitis.Datasheet [online].Encyclopedia Britannica. Encyclopedia Britannica Online. Encyclopedia Britannica, Inc. 2013 [retrieved on Nov. 2, 2013]. Retrieved from the Internet: <URL: http://www.britannica.com/EBchecked/topic/613180/ulcerative-colitis>.*
Lactobacillus.Datasheet [online].Encyclopedia Britannica. Encyclopedia Britannica Online. Encyclopedia Britannica, Inc. 2013 [retrieved on Nov. 2, 2013]. Retrieved from the Internet: <URL: http://www.britannica.com/EBchecked/topic/327373/Lactobacillus>.*
Takamura, T. et al. 2011 (published online Feb. 15, 2011). *Lactobacillus bulgaricus* OLL1181 activates the aryl hydrocarbon receptor pathway and inhibits colitis. Immunology and Cell Biology 89:817-822.*
van Baarlen, P. et al. 2009. Differential NF-kB pathways induction by *Lactobacillus plantarum* in the duodenum of healthy humans correlating with immune tolerance. Proceedings of the National Academy of Science (PNAS) 106(7): 2371-2376; specif. pp. 2371, 2375.*
Herías et al., Probiotic effects of *Lactobacillus casei* on DSS-induced ulcerative colitis in mice. Int J Food Microbiol. Aug. 25, 2005;103(2):143-55.
Kasai et al., DRESSA: biosensing of dioxin and dioxin-like chemicals using secreted alkaline phosphatase. Anal Biochem. Dec. 1, 2004;335(1):73-80.
Lee et al., Lactic acid bacteria inhibit proinflammatory cytokine expression and bacterial glycosaminoglycan degradation activity in dextran sulfate sodium-induced colitic mice. Int Immunopharmacol. Apr. 2008;8(4):574-80. doi: 10.1016/j.intimp.2008.01.009. Epub Feb. 5, 2008.
Martey et al., The aryl hydrocarbon receptor is a regulator of cigarette smoke induction of the cyclooxygenase and prostaglandin pathways in human lung fibroblasts. Am J Physiol Lung Cell Mol Physiol. Sep. 2005;289(3):L391-9.
Osman et al., Probiotics and blueberry attenuate the severity of dextran sulfate sodium (DSS)-induced colitis. Dig Dis Sci. Sep. 2008;53(9):2464-73. doi: 10.1007/s10620-007-0174-x. Epub Feb. 15, 2008.
Stenson, Prostaglandins and epithelial response to injury. Curr Opin Gastroenterol. Mar. 2007;23(2):107-10.
Takamura et al., Activation of the aryl hydrocarbon receptor pathway may ameliorate dextran sodium sulfate-induced colitis in mice. Immunol Cell Biol. Aug. 2010;88(6):685-9. doi:10.1038/icb.2010.35. Epub Mar. 16, 2010.

* cited by examiner

*Primary Examiner* — John S Brusca
*Assistant Examiner* — Sharon M Papciak
(74) *Attorney, Agent, or Firm* — Wolf, Greenfield & Sacks, P.C.

(57) ABSTRACT

The purpose of the present invention is to provide a probiotic (s) which can activate an aromatic hydrocarbon receptor (AhR) and can consequently prevent inflammatory damage in the digestive tract. The present invention relates to; a probiotic(s) capable of activating an AhR; an anti-inflammatory agent comprising the probiotic(s); an orally ingestible composition containing the anti-inflammatory agent; and a method for screening for the probiotic(s).

8 Claims, 5 Drawing Sheets

COMPOSITION FOR PREVENTING INFLAMMATIONS

RELATED APPLICATION

This application is a national stage filing under 35 U.S.C. §371 of international application PCT/JP2011/070436, filed Sep. 8, 2011, the disclosure of which is incorporated by reference herein in its entirety.

TECHNICAL FIELD

The present invention relates to a probiotic(s) and a novel strain that exhibit an inflammation-inhibiting effect in the intestines by activating the aryl hydrocarbon receptor (AhR), a composition for oral ingestion containing the probiotic(s) and the strain, and a method for screening the probiotic(s) and the strain.

BACKGROUND ART

For the development of today's medicine, the discovery and application of an antibiotic(s) have been important. However, in recent years, problems with side effects of antibiotics and the emergence of multi-drug-resistant microbes due to mutation have been much discussed. The idea of a 'probiotic(s)' as opposed to an 'antibiotic(s)' has recently been widely recognized in society. A probiotic(s) means 'a useful microorganism that improves the bacterial flora in the gastrointestinal tract and can bring a beneficial effect to a host, and a growth-promoting substance therefor', and the idea has been born of such a probiotic(s) being used so as to act on the flora (bacterial flora) in the gastrointestinal tract (intraoral or enteric) and preventing or improving a disease while making the flora healthier.

The aryl hydrocarbon receptor (AhR) is a transcription factor belonging to the bHLH-PAS family, appears to be expressed in most cells and tissue, and is known to activate the transcription of various genes by ligand binding. As a ligand for the AhR, a compound such as a dioxin or a polychlorinated biphenyl is known, but an endogenous ligand for the receptor is unknown.

The AhR in a state in which it is not bound to a ligand is inactive, and is present within cytoplasm being associated with a molecular chaperone such as Hsp90. When inactive AhR binds to a ligand, the molecular chaperone dissociates, and the activated AhR translocates into the nucleus. The AhR that has translocated into the nucleus is associated with a molecule called the ARNT (AhR Nucleus Translocator) to form a heterodimer, and interacts with an enhancer sequence called a xenobiotic responsive element (XRE) on DNA to thus activate the transcription of a downstream gene.

In recent years, it has been found that production of prostaglandin E2 (PGE2) is promoted by activation of an AhR pathway (Non-Patent Document 1) and that PGE2 is involved in protection against gastrointestinal damage (Non-Patent Document 2). Trials have therefore been started to see whether protection from gastrointestinal damage is possible by promoting the production of PGE2 by AhR activation.

As one of the trials, it has been reported that 2,3,7,8-tetrachlorodibenzo-p-dioxin (TCDD), which is known as an AhR ligand, suppresses the inflammatory response of ulcerative colitis induced by dextran sodium sulfate (DSS) (Non-Patent Document 3). This report discloses that in a DSS-treated mouse to which TCDD had been administered, compared with one to which TCDD had not been administered, weight loss, shortening of the intestinal tract, inflammation score, and the production of inflammatory cytokines were significantly suppressed.

PRIOR ART DOCUMENTS

Non-Patent Documents

[Non-Patent Document 1]
Stenson, W. F., Curr Opin Gastroenterol., 2007 March, 23(2): 107-10
[Non-Patent Document 2]
Martey, C. A. et al., Am J Physiol Lung Cell Mol Physiol, 289: L391-L399, 2005
[Non-Patent Document 3]
Takamura, T. et al., Immunology and Cell Biology (2010) 88, 685-689

SUMMARY OF THE INVENTION

Problems to be Solved by the Invention

It is an object of the present invention to provide a probiotic(s) that can suppress inflammatory damage in the gastrointestinal tract by activating the AhR.

Means for Solving the Problems

While carrying out research into the treatment of inflammatory disease in the gastrointestinal tract, the present inventors noticed that in a symptomatic therapy by administration of a steroid, a non-steroidal anti-inflammatory agent, etc., a complete treatment could not be carried out, and there were concerns about problems with side effects, etc, in long-term treatment; while continuing an investigation into a new treatment method, attention has been focused on the possibility of protection against gastrointestinal damage by AhR activation becoming a new treatment method.

However, the ligands for AhR that have currently been reported have strong toxicity and are unsuitable as anti-inflammatory agents, and there has to be confronted the new task of finding a novel anti-inflammatory agent that can exhibit an anti-inflammatory effect by activating the AhR and that can be taken safely. While continuing an intensive investigation, the present inventors have focused on a probiotic(s) that can alleviate symptoms and prolong a remission stage by acting on the flora in the gastrointestinal tract to thus improve the enteric environment, but there has to be confronted the further problem that a probiotic(s) having AhR-activating potency has not so far been reported, and the existence of such has yet to be established.

While continuing with further research, a new method has been found for screening strains having AhR-activating potency, isolation of a probiotic(s) having AhR-activating potency has been carried out successfully by this method, and the present invention has thus been accomplished. As hereinbefore described, a probiotic(s) having AhR-activating potency has hitherto not been known at all, and the existence of such a probiotic(s) is a surprising finding.

That is, the present invention relates to the following.
(1) A probiotic(s) having aryl hydrocarbon receptor (AhR) activating potency.
(2) The probiotic(s) according to (1), wherein the probiotic(s) is selected from the group consisting of a lactic acid bacterium, a *Bifidobacterium*, and a Propionic acid bacterium.
(3) The probiotic(s) according to (1) or (2), wherein the probiotic(s) is a lactic acid bacterium.

(4) *Lactobacillus delbrueckii* subsp. *bulgaricus* OLL1181 strain (depository number: FERM BP-11269).

(5) An anti-inflammatory agent containing a probiotic(s) having AhR-activating potency.

(6) The anti-inflammatory agent according to (5), wherein the probiotic(s) having AhR-activating potency is selected from the group consisting of a lactic acid bacterium, a *Bifidobacterium* and a Propionic acid bacterium.

(7) The anti-inflammatory agent according to (5) or (6), wherein the probiotic(s) having AhR-activating potency is a lactic acid bacterium.

(8) The anti-inflammatory agent according to any one of (5) to (7), wherein the probiotic(s) having AhR-activating potency is *Lactobacillus delbrueckii* subsp. *bulgaricus* OLL1181 strain.

(9) A composition for oral ingestion, containing the anti-inflammatory agent according to any one of (5) to (8).

(10) The composition for oral ingestion according to (9), wherein the composition for oral ingestion is selected from the group consisting of a drink composition, a food composition, a feedstuff composition, and a pharmaceutical composition.

(11) A method for screening a probiotic(s) having AhR-activating potency, the method including a step of stimulating AhR-expressing cells having an expression unit containing a xenobiotic responsive element (XRE) and a reporter gene region downstream thereof by means of a candidate probiotic(s) and/or a culture supernatant thereof.

Effects of the Invention

In accordance with the present invention, it is possible to produce an anti-inflammatory agent that can safely be taken orally and that can exhibit an anti-inflammatory effect by activating the AhR in the gastrointestinal tract with few side effects. Furthermore, since the probiotic(s) of the present invention has a clear site of action, in that an anti-inflammatory effect can be induced by acting on the AhR, a very high effect can be expected, and all of the probiotic(s) selected by the screening method of the present invention can be expected to have high potency in terms of the anti-inflammatory effect via AhR activation.

Furthermore, applying the anti-inflammatory effect of the probiotic(s) of the present invention not only enables long-term treatment to be carried out for an intractable disease such as an inflammatory bowel disease, for which there are difficulties with conventional anti-inflammatory agents from the viewpoint of side effects, etc., but also suggests the new possibility that a complete treatment is possible by improvement of the bodily constitution by utilizing homeostasis in a living body in the treatment of an inflammatory gastrointestinal tract disease for which only a symptomatic therapy involving suppressing inflammation at the site of inflammation by means of a medicinal agent is conventionally possible.

MODES FOR CARRYING OUT THE INVENTION

Figure 1:
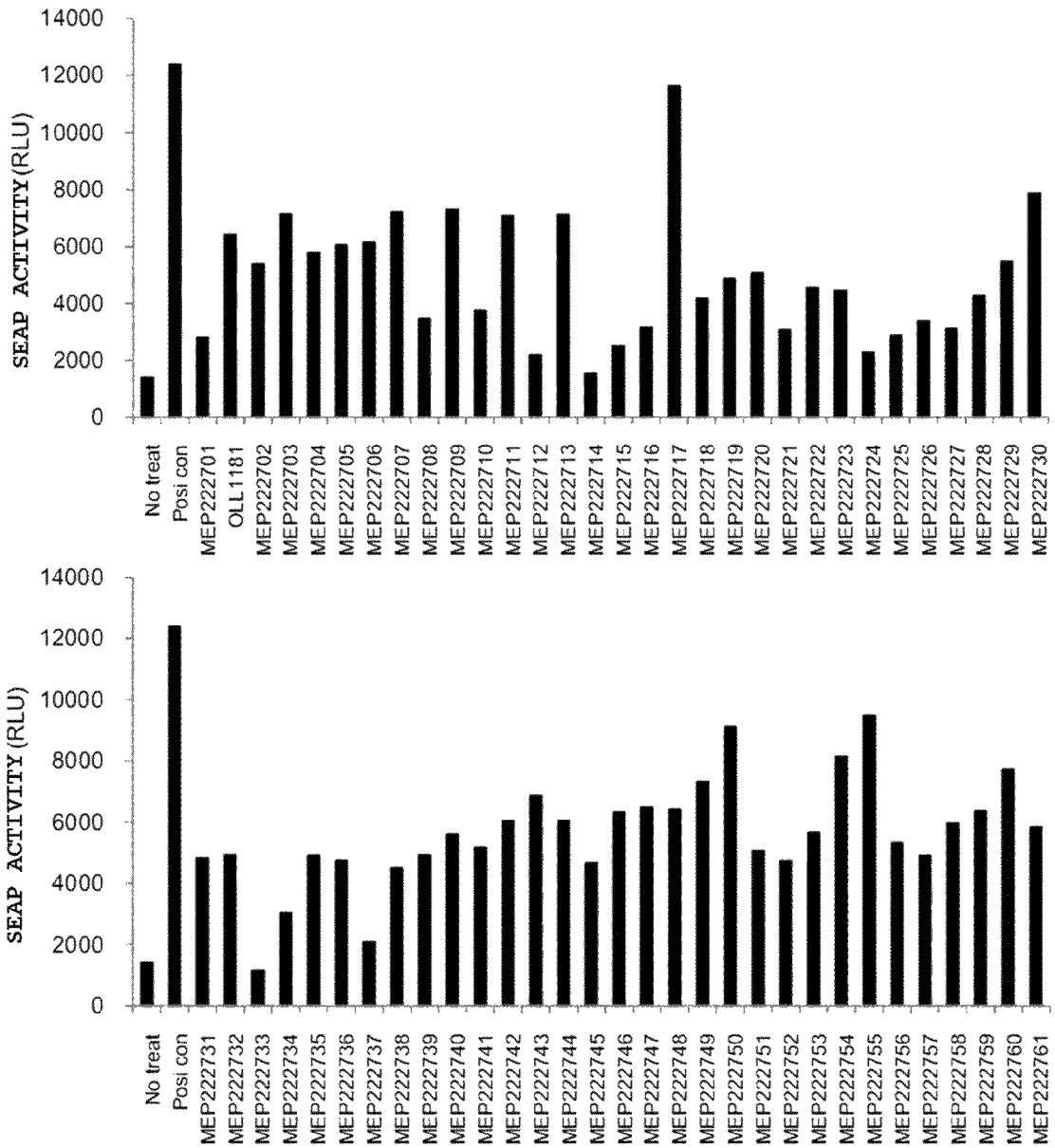
FIG. 1 shows the result of screening various types of lactic acid bacteria by the screening method of the present invention. In the figure, 'No treat' means a negative control and 'Posicon' means a positive control.

The present invention relates to a probiotic(s) having aryl hydrocarbon receptor (AhR) activating potency.

In the present invention, 'AhR-activating potency' means potency in being able to activate a signaling pathway that is initiated by AhR activation, and may involve any kind of activating mechanism. Therefore, it is not always necessary for a microbial body itself to be an AhR ligand, and for example a secretory substance produced by a microbe may have AhR-activating potency, or the AhR may be activated by a dead microbial body or homogenate thereof. Therefore, when a 'microorganism' or 'bacterium' is referred to or a specific microbe is referred to in the present invention, they include not only a living microbe but also a dead microbial body or homogenate thereof and a culture of said microbe or a secretory substance. However, it is preferably a microbial body itself such as a living microbe or a dead microbial body or homogenate thereof, and from the viewpoint of being capable of forming bacterial flora in the gastrointestinal tract, it is more preferably a living microbe.

In the present invention, the 'probiotic(s)' means, as described above, a 'useful microorganism(s) that improves the bacterial flora in the gastrointestinal tract and can bring a beneficial action to the host, and a growth-promoting substance(s) therefor'. Therefore, the probiotic(s) of the present invention includes not only a bacterium forming the bacterial flora but also a substance that promotes the growth of such a bacterium. Furthermore, the 'probiotic(s)' in the present invention includes useful microorganism(s) that can bring a beneficial action to a host and substance(s) produced by these microorganisms (microorganism culture). A growth-promoting substance having AhR-activating potency includes a case in which the substance itself has AhR-activating potency and also a case in which the substance itself does not have AhR-activating potency but it promotes growth of a bacterium having AhR-activating potency. Because of a suitable enteric environment being formed and the action being independent of differences in enteric environment between individuals, the probiotic(s) is preferably a living microbe, but when temporary AhR activation is desired, a dead microbial body, a microbial secretory substance, etc. are preferable.

Examples of microbes included in the probiotic(s) of the present invention include, but are not limited to, lactic acid bacterium, *Bifidobacterium*, Propionic acid bacterium, *Bacteroides, Eubacterium*, anaerobic *Streptococcus, Enterococcus*, and *Escherichia coli*. However, from the viewpoint of safety, etc., lactic acid bacterium, *Bifidobacterium*, and Propionic acid bacterium are preferable, and lactic acid bacterium and *Bifidobacterium* are more preferable. Among them, from the viewpoint of a microbial body itself having AhR-activating potency and the possibility of the AhR being activated not only by a living microbe but also by a dead microbial body, a lactic acid bacterium is yet more preferable. Among lactic acid bacteria, from the viewpoint of use in the production of yogurt and ease of application as a food, *Lactobacillus bulgaricus*, *Streptococcus thermophilus*, etc. are particularly preferable.

In recent years, it has been reported that, as a result of being stimulated by a lipopolysaccharide (LPS), the AhR binds Stat1 and suppresses transactivation of NF-κB (Kimura, A. et al., J Exp Med. 2009 Aug. 31; 206(9): 2027-35). However, the finding that gram-positive bacteria such as lactic acid bacteria, Bifidobacteria, or Propionic acid bacteria, which do not have an LPS in the cell membrane structure, have an AhR-activating potency is novel.

As a result of research by the present inventors, as a novel probiotic(s) having AhR-activating potency, *Lactobacillus delbrueckii* subsp. *bulgaricus* OLL1181 strain (depository number: FERM BP-11269) has been isolated. Therefore, in one embodiment of the present invention, the probiotic(s) of the present invention includes *Lactobacillus delbrueckii* subsp. *bulgaricus* OLL1181 strain.

The OLL1181 strain of the present invention has been deposited with the International Patent Organism Depository, National Institute of Technology and Evaluation (IPOD-NITE), having an address at #120, 2-5-8 Kazusakamatari, Kisarazu-shi, Chiba 292-0818, Japan, with the depository number: FERM BP-11269 dated 16 Jul. 2010, and is a novel *Lactobacillus delbrueckii* subsp. *Bulgaricus* having the following characteristics.
(a) Morphological characteristics
Bacillus
(b) Cultural characteristics
Medium name: Lactobacilli MRS Broth (Difco, Ref. No. 288130)
pH: not adjusted
Culturing temperature: 37° C.
Culturing time: 18 hours
(1) Shape: circular
(2) Diameter: 1 to 2 mm
(3) Color tone: white
(4) Raised state: hemispherical
(5) Peripheral edge: entire edge
(6) Surface form: smooth
(7) Transparency: opaque
(8) Viscosity: butter-like
(c) Physiological characteristics
(1) Gram staining: positive
(2) Lactic acid fermentation: homolactic fermentation
(3) Oxygen requirement: facultatively anaerobic
(4) Growth temperature: 15° C.+, 45° C.−

OLL1181 strain activates the AhR and increases the production of PGE2 on the downstream side of its signaling pathway, and as a result it can exhibit an anti-inflammatory effect in the gastrointestinal tract. From research by the present inventors it has been found that OLL1181 strain has AhR-activating potency both as a living microbe and a dead microbial body. It is a surprising finding that a microbial body of the OLL1181 strain, which is a gram-positive bacterium having no LPS, has AhR-activating potency. Furthermore, since the OLL1181 strain is *Lactobacillus delbrueckii* subsp. *Bulgaricus* and is a safe microbe having no biological toxicity, it is very useful as a probiotic(s) in terms of being able to be used in various applications including compositions for oral ingestion such as a food composition or a drink composition. Moreover, with regard to the OLL1181 strain, since the microbial body itself can activate the AhR, AhR-activating potency can be exhibited regardless of the viability of the microbe contained in a composition. Therefore, it is also very useful in terms of being able to be contained in various compositions.

The probiotic(s) of the present invention has AhR-activating potency and promotes the production of PGE2 by activating the AhR, and as a result an anti-inflammatory effect can be exhibited. Therefore, the probiotic(s) of the present invention can be used as an active ingredient of an anti-inflammatory agent. When the probiotic(s) of the present invention is used as an active ingredient of an anti-inflammatory agent, it is possible to use a living microbe, a dead microbe, a culture, a processed substance thereof, and a combination thereof. The culture means a substance using a culture supernatant or a medium component as it is after completing culturing of the probiotic(s) of the present invention, and the processed substance is not particularly limited as long as it is derived from the culture, examples thereof including those obtained from the culture by processing such as concentrating, making into a paste, spray-drying, freeze-drying, vacuum-drying, drum-drying, liquefying, diluting, or homogenizing. These processing procedures may be carried out by known methods as appropriate. The culture or the processed substance may contain a microbial body and/or homogenate thereof, and when a microbial body is contained it may be a living microbe or a dead microbe. From the viewpoint of improving the enteric environment by suppressing the growth of harmful intestinal bacteria by ingestion, it is contained in a composition as a living microbe. Furthermore, in addition to the probiotic(s) of the present invention, the anti-inflammatory agent may further contain, but is not limited to, any component such as a pharmaceutically acceptable carrier, excipient, additive, or diluent.

Furthermore, the probiotic(s) of the present invention, a culture thereof, or a processed substance thereof may be mixed with, as appropriate, for example, a medium component, an additive suitable for oral or tube ingestion, a solvent such as water, and any component such as a carbohydrate, a protein, a lipid, a vitamin, a biologically essential trace metal, a fragrance, a pharmaceutically acceptable carrier, or a food additive, thus giving a pharmaceutical composition, a food composition, etc.

The anti-inflammatory agent of the present invention can exhibit an anti-inflammatory effect due to promotion of the production of PGE2, and the anti-inflammatory agent of the present invention can therefore be used for the treatment, improvement and/or prevention of an inflammatory disease. Such an inflammatory disease may be any inflammatory disease, but because of the effect of the probiotic(s), which is the active ingredient, being able to be maximized, that is, the action on a local inflammatory site, the effect in improving other aggravating factors, etc. can be maximized, it is preferably used for, but is not limited to, inflammation of the gastrointestinal tract such as for example an inflammatory bowel disease.

As the probiotic(s) that can be contained in the anti-inflammatory agent of the present invention, from the viewpoint of ease of oral ingestion, the level of effect on the bacterial flora in the gastrointestinal tract, etc, it is preferably a lactic acid bacterium, a *Bifidobacterium*, or a Propionic acid bacterium, and more preferably a lactic acid bacterium or a *Bifidobacterium*. From the viewpoint of the effect on AhR activation that the microbial body itself has, it is more preferably a *Lacto-*

*bacillus*, and most preferably *Lactobacillus delbrueckii* subsp. *bulgaricus* OLL1181 strain.

Since the anti-inflammatory agent of the present invention is an agent that can exhibit as symptomatic therapy an effect on inflammation of the gastrointestinal tract, in particular the intestine, by acting on cells in the gastrointestinal tract, and that can exhibit as a complete treatment an effect by acting on the bacterial flora in the gastrointestinal tract, it is preferably ingested orally. Therefore, a composition for oral ingestion containing the anti-inflammatory agent of the present invention is also included in the present invention.

The amount ingested per day of the probiotic(s), anti-inflammatory agent, or composition for oral ingestion of the present invention is not particularly limited and may be appropriately adjusted according to age, symptoms, body weight, intended application, etc. For example, the amount ingested per day as the probiotic(s) is typically 0.01 to $100 \times 10^{11}$ cells/body, preferably 0.1 to $10 \times 10^{11}$ cells/body, and more preferably 0.3 to $5 \times 10^{11}$ cells/body. Furthermore, for example, the amount ingested per day as the probiotic(s) is 0.01 to $100 \times 10^{11}$ cells/60 kg body weight, preferably 0.1 to $10 \times 10^{11}$ cells/60 kg body weight, and more preferably 0.3 to $5 \times 10^{11}$ cells/60 kg body weight.

However, the amounts ingested of the probiotic(s), anti-inflammatory agent, or the composition for oral ingestion of the present invention is not limited to the values cited above.

The content of the probiotic(s) contained in the anti-inflammatory agent or composition for oral ingestion of the present invention may be determined as appropriate depending on its application form. Typically, as probiotic(s) dry microbial body it is for example 5 to 50 w/w %, preferably 1 to 75 w/w %, and more preferably 0.1 to 100 w/w % and 1 to 100 w/w %.

However, the content of the probiotic(s) contained in the anti-inflammatory agent or composition for oral ingestion of the present invention is not limited to the values cited above.

In the present specification, a 'composition for oral ingestion' means any composition that can be ingested orally. Therefore, examples of the composition for oral ingestion include, but are not limited to, a drink composition, a food composition, a feedstuff composition, and a pharmaceutical composition.

The drink composition of the present invention typically contains one or more selected from a probiotic(s) having AhR-activating potency, a culture thereof, and a processed product thereof. The drink composition of the present invention may further contain a carbohydrate, a protein, a lipid, a vitamin, a biologically essential trace metal (manganese sulfate, zinc sulfate, magnesium chloride, potassium carbonate, etc.), a fragrance, or another component, as long as growth of the probiotic(s) is not inhibited. Such a drink composition improves the enteric environment of an ingesting individual and exhibits an effect in improving and/or preventing an inflammatory disease.

The food composition of the present invention typically contains one or more selected from a probiotic(s) having AhR-activating potency, a culture thereof, and a processed product thereof. The food composition of the present invention may further contain a carbohydrate, a protein, a lipid, a vitamin, a biologically essential trace metal (manganese sulfate, zinc sulfate, magnesium chloride, potassium carbonate, etc.), a fragrance, or another component, as long as growth of the probiotic(s) is not inhibited. Such a food composition improves the enteric environment of an ingesting individual and exhibits an effect in improving and/or preventing an inflammatory disease.

Examples of the carbohydrate include a saccharide, a modified starch (dextrin, soluble starch, British starch, oxidized starch, a starch ester, a starch ether, etc.), and dietary fiber.

Examples of the protein include whole milk powder, skimmed milk powder, partly skimmed milk powder, casein, whey powder, whey protein, whey protein concentrate, whey protein isolate, α-casein, β-casein, κ-casein, β-lactoglobulin, α-lactoalbumin, lactoferrin, animal and plant proteins such as soybean protein, egg protein, and meat protein, hydrolysates thereof; and various types of milk-derived components such as butter, whey mineral, cream, whey, non-protein nitrogen, sialic acid, phospholipid, and lactose.

Examples of the lipid include animal oils and fats such as lard and fish oil, and fractionated oil, hydrogenated oil, and ester exchanged oil therefrom; and plant oils and fats such as palm oil, safflower oil, corn oil, rapeseed oil, and coconut oil, and fractionated oil, hydrogenated oil, and ester exchanged oil therefrom.

Examples of the vitamin include vitamin A, a carotene, the vitamin B group, vitamin C, the vitamin D group, vitamin E, the vitamin K group, vitamin P, vitamin Q, niacin, nicotinic acid, pantothenic acid, biotin, inositol, choline, and folic acid, and examples of the mineral include calcium, potassium, magnesium, sodium, copper, iron, manganese, zinc, and selenium.

The category or type of the drink composition and the food composition of the present invention are not limited, and they may be functional food, food for specified health use, food for specialized applications, food with nutrient function claims, health food, or nursing care food and, furthermore, confectionery, a lactic fermenting beverage, a dairy product such as cheese or yogurt, seasoning, etc. The food and drink form is not limited either; it may be in any food and drink form that can normally be distributed such as solid, liquid, fluid food, jelly, tablet, granule, or capsule form, and may be added to various types of food (cow's milk, soft drink, cultured milk, yogurt, cheese, bread, biscuit, cracker, pizza crust, powdered formula, liquid food, medical food, nutritive food, frozen food, processed food, other commercial food, etc.). Production of these foods and drinks may be carried out by standard methods of a person skilled in the art.

As hereinbefore described, the probiotic(s), culture thereof, or processed substance thereof of the present invention may also be processed into general food and drink including dairy products/cultured milk and may also be used as a starter in the production of dairy products/cultured milk, such as yogurt or cheese. When used as a starter, as long as there are no problems with the survival and growth of the probiotic(s) of the present invention and as long as there are no problems with the production of a dairy product, it may be mixed with another microorganism. For example, it may be mixed with *Lactobacillus delbrueckii* subsp. *bulgaricus, Streptococcus thermophilus, Lactobacillus acidophilus*, etc., which are the main bacterial species used as lactic acid bacteria for yogurt, or it may be used as a starter by mixing with another bacterial species generally used for yogurt or cheese. The production of dairy products/cultured milk using the starter may be carried out by a standard method. For example, plain yogurt may be produced by mixing the starter with milk or a dairy product that has been cooled after heating, mixing, homogenizing, and sterilizing, and by fermenting and cooling the mixture.

The feedstuff composition of the present invention typically contains one or more selected from a probiotic(s) having AhR-activating potency, a culture thereof, and a processed product thereof. The feedstuff composition of the present invention may further contain a carbohydrate, a protein, a lipid, a vitamin, a biologically essential trace metal (manganese sulfate, zinc sulfate, magnesium chloride, potassium carbonate, etc.), a fragrance, or another component, as long as growth of the probiotic(s) is not inhibited. Such a feedstuff composition improves the enteric environment of an ingesting individual and exhibits an effect in improving and/or preventing an inflammatory disease.

The pharmaceutical composition of the present invention typically contains one or more selected from a probiotic(s) having AhR-activating potency, a culture thereof, and a processed product thereof. Such a pharmaceutical composition improves the enteric environment of an ingesting individual and exhibits an effect in improving and/or preventing an inflammatory disease. Furthermore, with regard to such a pharmaceutical composition, the administration route is not particularly limited; oral or parenteral administration is included, and examples include oral administration, tube administration, and enteral administration. From the viewpoint of ease and safety, oral administration is preferable. The form of a preparation is not particularly limited, and may be selected as appropriate according to the administration route; examples include an aerosol, a liquid, an extract, an elixir, a capsule, granules, a pill, an eye ointment, a percutaneous absorption preparation, a suspension, an emulsion, a suppository, a powder, a spirit, a tablet, a syrup, an infusion, a decoction, an injection, a patch, a tincture, an eye dropper, a lozenge, an ointment, a poultice, an aromatic water, a liniment, a lemonade, a fluid extract, and a lotion.

With regard to the oral administration preparation, various known types of form of preparation may be used, and examples include granules, a powder, a tablet, a pill, a capsule, a liquid, a syrup, an emulsion, a suspension, and a lozenge. Furthermore, making it into an enteric-coated preparation enables it to be transported to the intestine more efficiently without being affected by stomach acid.

As an example of parenteral administration, administration in the form of an injection may be cited. Furthermore, the probiotic(s), culture thereof, or processed substance thereof of the present invention may be administered locally to a region that is to be treated. For example, it may be subjected to local infusion during an operation or administration using a catheter.

With regard to a carrier that can be used in the pharmaceutical composition of the present invention, a surfactant, an excipient, a colorant, a fragrance, a preservative, a stabilizer, a buffer, a suspension, an isotonizing agent, a binder, a disintegrant, a lubricant, a flowability promoter, a taste-masking agent, etc. can be cited as pharmaceutically acceptable carriers, and another commonly used carrier may be used as appropriate. Specific examples include light anhydrous silicic acid, lactose, microcrystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium chain fatty acid triglyceride, polyoxyethylene hardened castor oil 60, sucrose, carboxymethylcellulose, corn starch, and an inorganic salt.

The present invention has been accomplished based on the new finding that a probiotic(s) that can activate AhR exists, and the present invention therefore also includes a method for screening a probiotic(s) that has AhR-activating potency, a method for activating the AhR that includes administrating the screened probiotic(s) to a target, and a method for preventing and/or treating an inflammatory disease. In particular, the ability to screen for a probiotic(s) that can bring a beneficial action to an ingesting individual based on AhR-activating potency is not known at all in the art. In the present invention, the inflammatory disease may be either systemic or local, and an inflammation site may be any of skin, mucous membrane, a digestive organ, a respiratory organ, the liver, a blood vessel, the uterus, etc. Suitable examples of the inflammatory disease include, but are not limited to, an inflammatory bowel disease.

As described above, the AhR translocates into the nucleus when activated, and binds a xenobiotic responsive element (XRE, also called as dioxin responsive element: Dioxin Responsive Element, DRE) on DNA to thus cause expression of a gene on the downstream side thereof, such as for example Cytchrome P450 enzyme (CYP1A1). Therefore, it is possible to test whether or not a candidate probiotic(s) has AhR-activating potency by stimulating by means of the candidate probiotic(s) and/or a culture supernatant thereof. AhR-expressing cells having an expression unit including at least one XRE sequence and a reporter gene region on the downstream side thereof, and examining the expression of a reporter gene.

For example, an in vitro bioassay method involving screening of an AhR-activating compound using a chemical substance such as a dioxin or a PCB is known. The AhR-expressing cells that are used in the present invention may be any cells as long as they can be used in the bioassay. From the viewpoint of availability, ease of culturing, simplicity of a detection method, etc., HeXS34 cells, Caco-2 cells, etc. can preferably be cited. An expression unit containing XRE and a reporter gene on the downstream side thereof of such an AhR-expressing cell may be endogenous or may be introduced from the outside by means of transformation, etc. From the viewpoint of being specific to the assay, less detection noise, etc., an expression unit introduced from the outside is preferable.

As a reporter gene used in the present invention, any gene may be used as long as the amount expressed of protein and/or mRNA, which is a gene transcript, can be measured quantitatively. For example, it is possible to detect AhR-activating potency by quantitatively detecting the level of the above CYP1A1 expression using quantitative real-time PCR, etc. Examples thereof include a test system using Caco2 cells, which is described in Example 3, etc. of Experimental examples described later. It is of course possible to use any reporter gene that is known as one for a bioassay by a person skilled in the art; from the viewpoint of ease of quantitative determination, stability of expression, etc., examples include, but are not limited to, secreted alkali phosphatase (SEAP), secreted luciferase, green fluorescent protein (GFP), etc. As one example thereof, there can be cited a test system using HeXS34 cells described in Example 1, etc. of Experimental examples described later.

In the present invention, when a plasmid used for introducing the expression unit into cells from the outside is a plasmid containing at least one XRE sequence and a reporter gene on the downstream side thereof, this is called a xenobiotic responsive plasmid. When the reporter gene of the xenobiotic responsive plasmid is SEAP, the xenobiotic responsive plasmid may be expressed as pXRE-SEAP. Preparation of a xenobiotic responsive plasmid and introduction into a cell may be carried out in accordance with for example WO2005/113767, WO2007/004361, or an article by Kasai et al. (Kasai et al., Toxicol Appl Pharmacol. 2006; 211(1): 11-19).

In the screening method of the present invention, AhR-activating potency may be measured by stimulating AhR-expressing cells by means of a candidate probiotic(s) and/or a culture supernatant thereof and quantitatively determining the level of expression of a reporter gene present on the downstream side of the XRE sequence. It is suggested that the higher the level of reporter gene expression, the greater the AhR-activating potency. Therefore, as a screening method, after a candidate probiotic(s) and AhR-expressing cells are co-cultured, the level of reporter gene expression is measured and compared with the level of reporter gene expression in a negative control that has been measured in the same manner, and if it is significantly higher, it can be determined that the candidate probiotic(s) has AhR-activating potency.

In the present specification, 'stimulating' AhR-expressing cells typically means that AhR-expressing cells are incubated for a predetermined time in the presence of a candidate probiotic(s) and/or a culture supernatant thereof. Therefore, an embodiment of co-culturing AhR-expressing cells and the candidate probiotic(s) when the candidate probiotic(s) is a living microbe and an embodiment of incubating for a predetermined time in the presence of a dead microbial body, a secreted substance, homogenate, and/or a culture supernatant, etc. are included. The time for incubation may be selected as appropriate according to the candidate probiotic(s), the cells to be tested, the amount of AhR expressed, the type of reporter gene, etc.

The present invention is further explained below by reference to Examples, but such Examples are only illustrations of the present invention and do not limit the present invention.

EXAMPLES

In the Examples, all of the values obtained are expressed as average value±standard deviation. Furthermore, all of the statistical analyses were carried out using the unpaired Student's t test, and when $p<0.05$ it was determined that there was a significant difference.

Example 1

Screening of Lactic Acid Bacterium Having AhR-Activating Potency (1) Preparation of HeXS34 Cells Preparation of HeXS34 cells was carried out in accordance with a previous report (Kasai et al., Toxicol Appl Pharmacol. 2006; 211(1): 11-19). Briefly, HeXS34 cells were prepared by stably transforming xenobiotic responsive plasmid pXRE-SEAP, which had SEAP gene introduced thereinto downstream of 2 copies of XRE consensus sequence (tctcacgcaactccg), into Hepa-1c1c7 cells (mouse hepatoma cell line, American Type Culture Collection (Manassas, Va., USA)).

(2) Stimulation with Heat-Sterilized Lactic Acid Bacterium

The HeXS34 cells prepared in (1) maintained in MEMα medium (Invitrogen, Carlsbad, Calif.) supplemented with 10% fetal bovine serum (FBS) were sown on a 96 well plate at 5000 cells/90 μL per well, and cultured for 24 hours in the presence of and in the absence of 10 μL ($5 \times 10^9$ cells/mL) of a freeze-dried heat-sterilized lactic acid bacterium strain. As a positive control, 50 μM 2,3,7,8-tetrachlorodibenzodioxin (TCDD) was used. Furthermore, as a negative control, a well to which no lactic acid bacterium or TCDD was added was provided. Culture supernatants were subsequently subjected to an SEAP assay.

(3) SEAP Assay

The culture supernatant obtained in (2) was subjected to quantitative determination of SEAP by a chemiluminescence method using a Great EscAPe SEAP Chemiluminescence kit (Clontech). The assay was carried out three times, and the average value was determined using the luminescence intensity (LU) so obtained as the SEAP activity.

The results are shown in FIG. 1. In 47 strains, including the *Lactobacillus delbrueckii* subsp. *bulgaricus* OLL1181 strain, high SEAP activity was observed compared with the negative control.

Strains with MEP in the strain name are strains owned by Meiji Co., Ltd. Furthermore, the names of the bacterial species are as shown in the table below.

TABLE 1

| Strain name | Species name |
| --- | --- |
| MEP222701 | *Lactobacillus gasseri* |
| OLL1181 | *Lactobacillus delbrueckii* subsp. *bulgaricus* |
| MEP222702 | *Lactococcus lactis* subsp. *lactis* |
| MEP222703 | *Lactococcus lactis* subsp. *lactis* |
| MEP222704 | *Lactococcus lactis* subsp. *lactis* |
| MEP222705 | *Lactococcus lactis* subsp. *lactis* |
| MEP222706 | *Lactococcus lactis* subsp. *cremoris* |
| MEP222707 | *Lactococcus lactis* subsa. *lactis* |
| MEP222708 | *Lactococcus lactis* subsp. *lactis* |
| MEP222709 | *Lactococcus lactis* subsp. *lactis* |
| MEP222710 | *Streptococcus thermophilus* |
| MEP222711 | *Lactococcus lactis* subsp. *cremoris* |
| MEP222712 | *Lactococcus lactis* subsp. *cremoris* |
| MEP222713 | *Lactococcus lactis* subsp. *cremoris* |
| MEP222714 | *Streptococcus thermophilus* |
| MEP222715 | *Streptococcus thermophilus* |
| MEP222716 | *Streptococcus thermophilus* |
| MEP222717 | *Streptococcus thermophilus* |
| MEP222718 | *Lactococcus lactis* subsp. *lactis* |
| MEP222719 | *Lactococcus lactis* subsp. *lactis* |
| MEP222720 | *Lactococcus lactis* subsp. *lactis* |
| MEP222721 | *Lactococcus lactis* subsp. *lactis* |
| MEP222722 | *Lactococcus lactis* subsp. *lactis* |
| MEP222723 | *Lactococcus lactis* subsp. *lactis* |
| MEP222724 | *Lactococcus lactis* subsp. *lactis* |
| MEP222725 | *Lactococcus lactis* subsp. *lactis* |
| MEP222726 | *Lactococcus lactis* subsp. *lactis* |
| MEP222727 | *Lactococcus lactis* subsp. *lactis* |
| MEP222728 | *Lactococcus lactis* subsp. *lactis* |
| MEP222729 | *Lactococcus lactis* subsp. *cremoris* |
| MEP222730 | *Lactococcus lactis* subsp. *cremoris* |
| MEP222731 | *Lactococcus lactis* subsp. *lactis* |
| MEP222732 | *Lactococcus lactis* subsp. *lactis* |
| MEP222733 | *Lactococcus lactis* subsp. *lactis* |
| MEP222734 | *Lactococcus lactis* subsp. *lactis* |
| MEP222735 | *Lactococcus lactis* subsp. *cremoris* |
| MEP222736 | *Lactococcus lactis* subsp. *cremoris* |
| MEP222737 | *Streptococcus thermophilus* |
| MEP222738 | *Lactococcus lactis* subsp. *cremoris* |
| MEP222739 | *Lactococcus lactis* subsp. *cremoris* |
| MEP222740 | *Lactococcus lactis* subsp. *cremoris* |
| MEP222741 | *Lactococcus lactis* subsp. *cremoris* |
| MEP222742 | *Lactococcus lactis* subsp. *cremoris* |
| MEP222743 | *Lactococcus lactis* subsp. *cremoris* |
| MEP222744 | *Lactococcus lactis* subsp. *cremoris* |
| MEP222745 | *Lactococcus lactis* subsp. *cremoris* |
| MEP222746 | *Lactococcus lactis* subsp. *cremoris* |
| MEP222747 | *Lactococcus lactis* subsp. *cremoris* |
| MEP222748 | *Lactococcus lactis* subsp. *cremoris* |
| MEP222749 | *Lactococcus lactis* subsp. *cremoris* |
| MEP222750 | *Lactococcus lactis* subsp. *cremoris* |
| MEP222751 | *Lactococcus lactis* subsp. *cremoris* |
| MEP222752 | *Lactococcus lactis* subsp.*cremoris* |
| MEP222753 | *Lactococcus lactis* subsp. *cremoris* |
| MEP222754 | *Lactococcus lactis* subsp. *cremoris* |
| MEP222755 | *Lactococcus lactis* subsp. *cremoris* |
| MEP222756 | *Lactococcus lactis* subsp. *cremoris* |
| MEP222757 | *Lactococcus lactis* subsp. *cremoris* |
| MEP222758 | *Lactococcus lactis* subsp. *cremoris* |
| MEP222759 | *Lactococcus lactis* subsp. *cremoris* |
| MEP222760 | *Lactococcus lactis* subsp. *cremoris* |
| MEP222761 | *Lactobacillus delbrueckii* subsp. *bulgaricus* |

Example 2

SEAP Activity Inhibition by αNF

From the screening in Example 1, the OLL1181 strain was selected as a candidate strain having AhR-activating potency, the MEP222701 strain was selected as a negative control having no AhR-activating potency, and they were subjected to further experiments. In the same way as for Example 1, stimulation was carried out for 24 hours using heat-sterilized suspensions of the two types of lactic acid bacterium strains ($5 \times 10^9$ cells/mL solution was added at 5% v/v and 10% v/v), and the culture supernatant was subjected to SEAP assay. Furthermore, in order to clearly show that AhR acted on activation of an XRE region, HeXS34 cells that had been preincubated for 30 minutes with 10 μM α-naphthoflavone (αNF, AhR antagonist) prior to stimulation by the lactic acid bacterium and HexS34 cells that had not been preincubated were used, stimulation was carried out for 24 hours with a 10% v/v heat-sterilized OLL1181 strain suspension, and the culture supernatant was then subjected to SEAP assay in the same way as for Example 1. (3).

Figure 2:
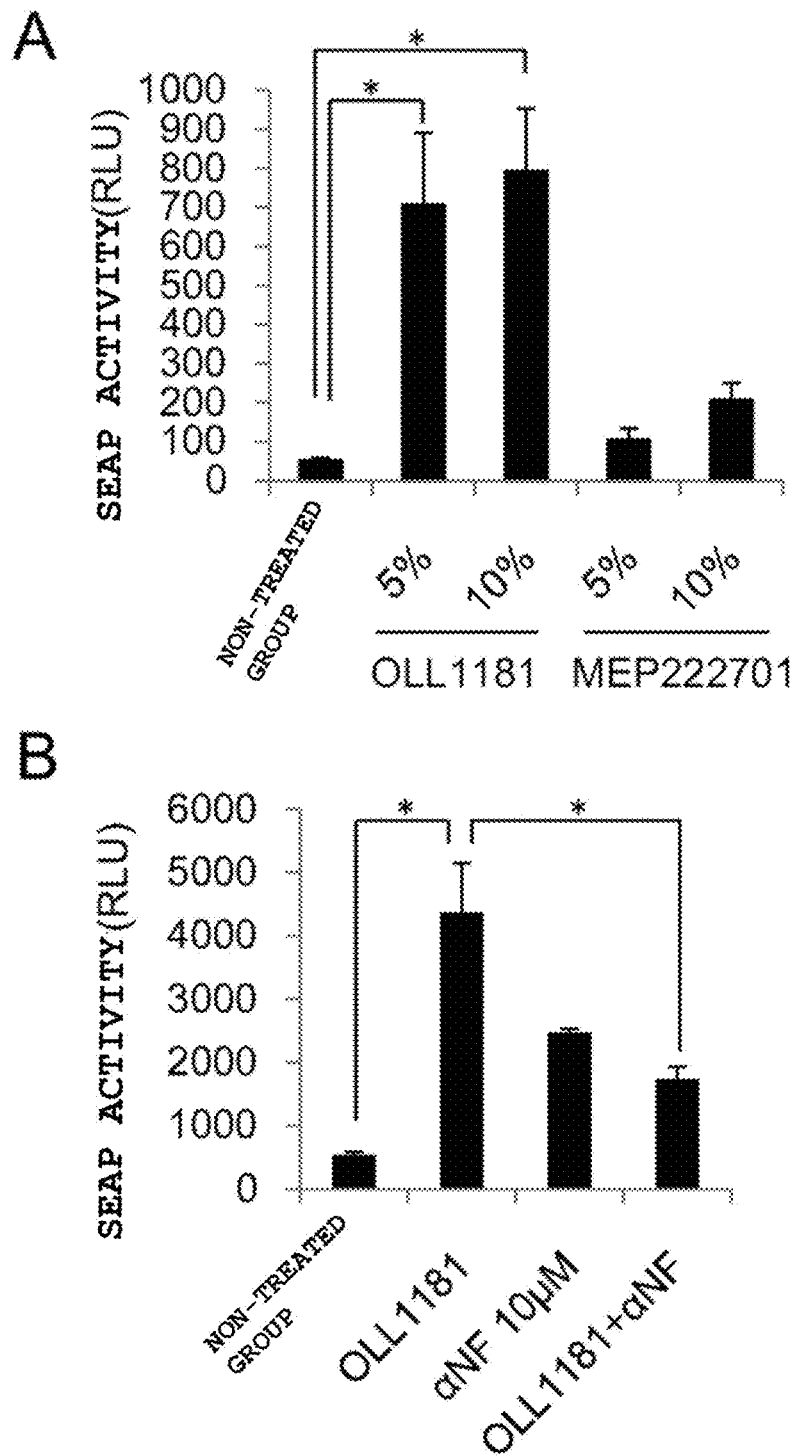
FIG. 2 shows the result of SEAP activation in a culture supernatant of HeXS34 cells stimulated by OLL1181 strain, which is the strain of the present invention.

The results are shown in FIG. 2. A is a graph comparing the OLL1181 strain and the MEP222701 strain in terms of SEAP activity, and with regard to the OLL1181 strain, the SEAP activity significantly increased for both 5% v/v ($2.5 \times 10^8$ cells/mL well) and 10% v/v ($5 \times 10^8$ cells/mL well) added amounts of lactic acid bacterium strain suspension compared with an untreated region. B is a graph comparing one that had been preincubated with αNF and one that had not been preincubated in an amount of lactic acid bacterium strain suspension added of 10% v/v ($5 \times 10^8$ cells/mL well) and one that had been preincubated with αNF significantly inhibited the increase in SEAP activity caused by stimulation with the OLL1181 strain, compared with one that had not been preincubated. From this result it is surmised that the increase in SEAP activity by stimulation with the OLL1181 strain is due to activation of the XRE sequence by AhR activation.

Example 3

Verification of AhR-Activating Potency Using Caco2 Cells (1) Stimulation of Caco2 Cells Verification of AhR-activating potency was carried out using Caco2 cells, which are human colon cancer-derived cells. Human Caco2 cells were cultured in DMEM medium (Invitrogen/Gibco, Carlsbad, Calif.) supplemented with 10% FBS and an antibiotic, a portion was preincubated with 5 μM αNF for 30 minutes, and both that which had been preincubated and that which had not been preincubated were subjected to stimulation with a 10% v/v heat-sterilized OLL1181 strain suspension for 4 hours.

(2) Quantitative Real-Time PCR

The Caco2 cells obtained in (1) were subjected to quantitative real-time PCR. The quantitative real-time PCR was carried out using an ABI 7300 real-time PCR system (Applied Biosystems, Foster City, Calif.) in accordance with an instruction manual. With regard to a primer and a probe, those for human CYP1A1 (Assay ID: Hs02382618_s1) and those for glyceraldehyde-3-phosphate dehydrogenase (GAPDH) (Assay ID: Hs99999905_m1) (Applied Biosystems) were used. The level of CYP1A1 gene expression relative to the level of GAPDH gene expression was calculated and defined as the relative level of CYP1A1 gene expression.

Figure 3:
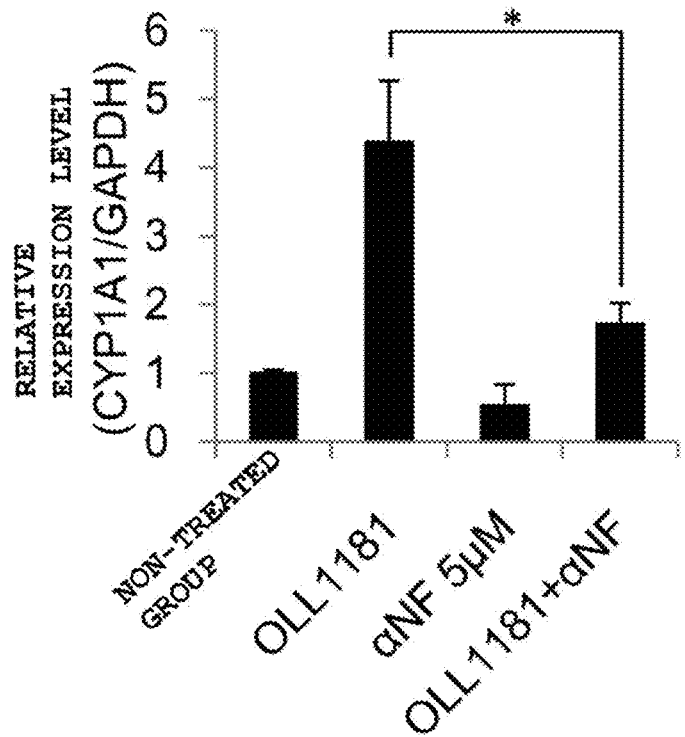
FIG. 3 shows the relative level of CYP1A1 expression in Caco2 cells stimulated by the OLL1181 strain of the present invention. The relative levels of expression when stimulated only with MEP222701 strain and only with αNF are shown together for comparison.

The results are shown in FIG. 3. Due to stimulation by the OLL1181 strain, CYP1A1 expression was significantly increased, and such increase of expression was significantly suppressed by αNF. Therefore, it can be seen that in the human colon cells AhR activation by the OLL1181 strain occurred.

Example 4

In Vivo Activation of AhR

200 μL of a heat-sterilized OLL1181 strain suspension, a heat-sterilized MEP222701 strain suspension ($5 \times 10^9$ cells/mL), and PBS were orally administered to 4 to 6 week old C57BL/6 mice (female, body weight 14 to 18 g, purchased from Japan SLC, Inc.) via a stomach tube. The dose of each strain administered corresponded to $1 \times 10^9$ cells/body. 4 hours after administration, the large intestine was cut out, and in the same way as for Example 3. (2) the relative level of CYP1A1 expression was quantitatively determined by quantitative real-time PCR using primers and probes for mouse CYP1A1 (Assay ID: Mm00487218_m1) and for GAPDH (Assay ID: Mm99999915_g1).

Figure 4:
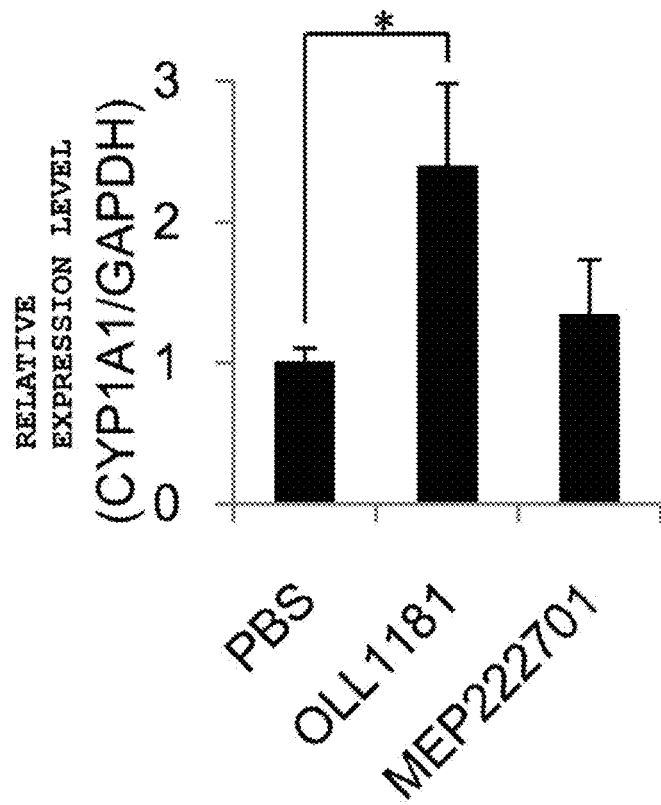
FIG. 4 shows the relative level of CYP1A1 expression in vivo in the large intestine when OLL1181 strain, which is the strain of the present invention, is administered to a mouse.

The results are shown in FIG. 4. In the group to which the suspension of the OLL1181 strain was administered, the level of CYP1A1 expression significantly increased compared with the PBS-administered group, but in the MEP222701 strain-administered group there was no significant difference from the PBS-administered group. This shows that AhR activation also occurred in vivo in the large intestine by oral administration of the OLL1181 strain.

Example 5

Induction of COX2 Expression In Vitro and In Vivo and Induction of Production of Prostaglandin E2

(1) Verification of Induction of COX-2 Expression

In order to verify that COX-2 expression was induced as a result of AhR activation by stimulation with OLL1181 strain, and that production of prostaglandin E2 from arachidonic acid was thereby facilitated, expression of COX-2 in vitro and in vivo was confirmed by the same method as in Example 3 and Example 4 except that as a primer and a probe for quantitative real-time PCR those for human and mouse COX-2 (for human, Assay ID: Hs01573469_m1, for mouse, Assay ID: Mm01307334_g1) and for GAPDH were used. The level of COX-2 gene expression relative to the level of GAPDH gene expression was calculated and defined as the relative level of COX-2 gene expression.

(2) Prostaglandin E2(PGE2) ELISA

Human Caco2 cells were stimulated in the same way as for Example 3 (1) except that as the lactic acid bacterium for stimulation, in addition to OLL1181 and MEP222701, MEP222761, which showed high AhR activity in the screening of Example 1, was also used, and the stimulation time was 24 hours; the amount of PGE2 secreted in the culture supernatant was quantitatively determined using a PGE2 Competitive ELISA kit (Thermo Scientific inc., Waltham, Mass.) in accordance with an instruction manual.

Figure 5:
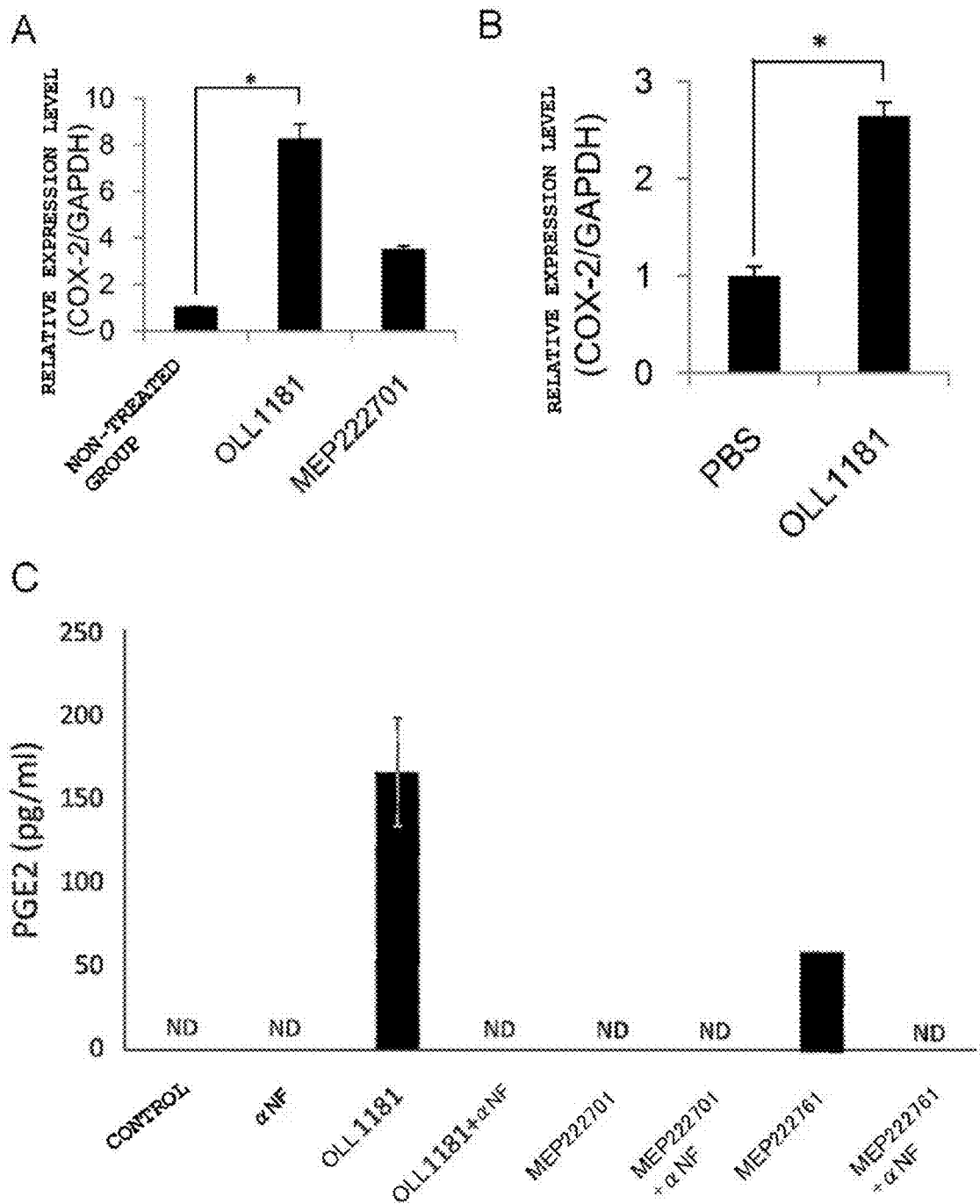
FIG. 5 shows, when stimulated with OLL1181 strain, which is the strain of the present invention, A: relative level of COX-2 expression in human Caco2 cells, B: relative level of COX-2 expression in vivo in the mouse large intestine, and C: amount of PGE2 secreted in a culture supernatant of human Caco2 cells.

The results are shown in FIG. 5. A denotes the relative level of COX-2 expression in vitro in human Caco2 cells, B denotes the relative level of COX-2 expression in vivo in mouse large intestine, and C denotes the amount of PGE2 produced in human Caco2 cells. It was confirmed that as a result of stimulation with the OLL1181 strain, COX-2 expression significantly increased both in human in vitro and in mouse in vivo compared with the negative control. Furthermore, in human Caco2 cells, production of PGE2 by stimulation with the OLL1181 strain was confirmed. Since such production of PGE2 was inhibited by αNF, it was confirmed that the PGE2 production was due to AhR activation.

Example 6

AhR Activation by OLL1181 Strain Alleviates DSS-Induced Enteritis

In order to induce enteritis, 4 to 6 week old C57BL/6 mice (female, body weight 14 to 18 g, purchased from Japan SLC, Inc.) were made to freely ingest 3% dextran sodium sulfate (DSS, molecular weight 5000, purchased from Wako Pure Chemical Industries, Ltd.) dissolved in drinking distilled water every day for 7 days, and were then made to freely ingest distilled water free from DSS for 3 days. In order to verify an effect of alleviation by the strain, heat-sterilized OLL1181 strain, MEP222701 strain, and MEP222761 strain were orally administered every day for 7 days at 200 μL ($5 \times 10^9$ cells/mL) via a stomach tube. The dose of each strain administered corresponded to $1 \times 10^9$ cells/body. As a control, 200 μL of PBS was orally administered every day for 7 days instead of the bacterial solution. Furthermore, 200 μL of PBS was orally administered every day for 7 days to a non-colitis-induced group to which no DSS was administered. The experiment was carried out with n=10 to 12 for each group, the large intestine was cut out on the $11^{th}$ day after starting DSS administration, the length of the large intestine was measured, and the amounts of TNF-α and MPO expressed were quantitatively determined by quantitative real-time PCR using a primer and a probe for mouse TNF-α (Assay ID: Mm00443258_m1) and for mouse myeloperoxidase (MPO) (Assay ID: Mm00447886_m1) in the same way as for Example 3. (2).

Figure 6:
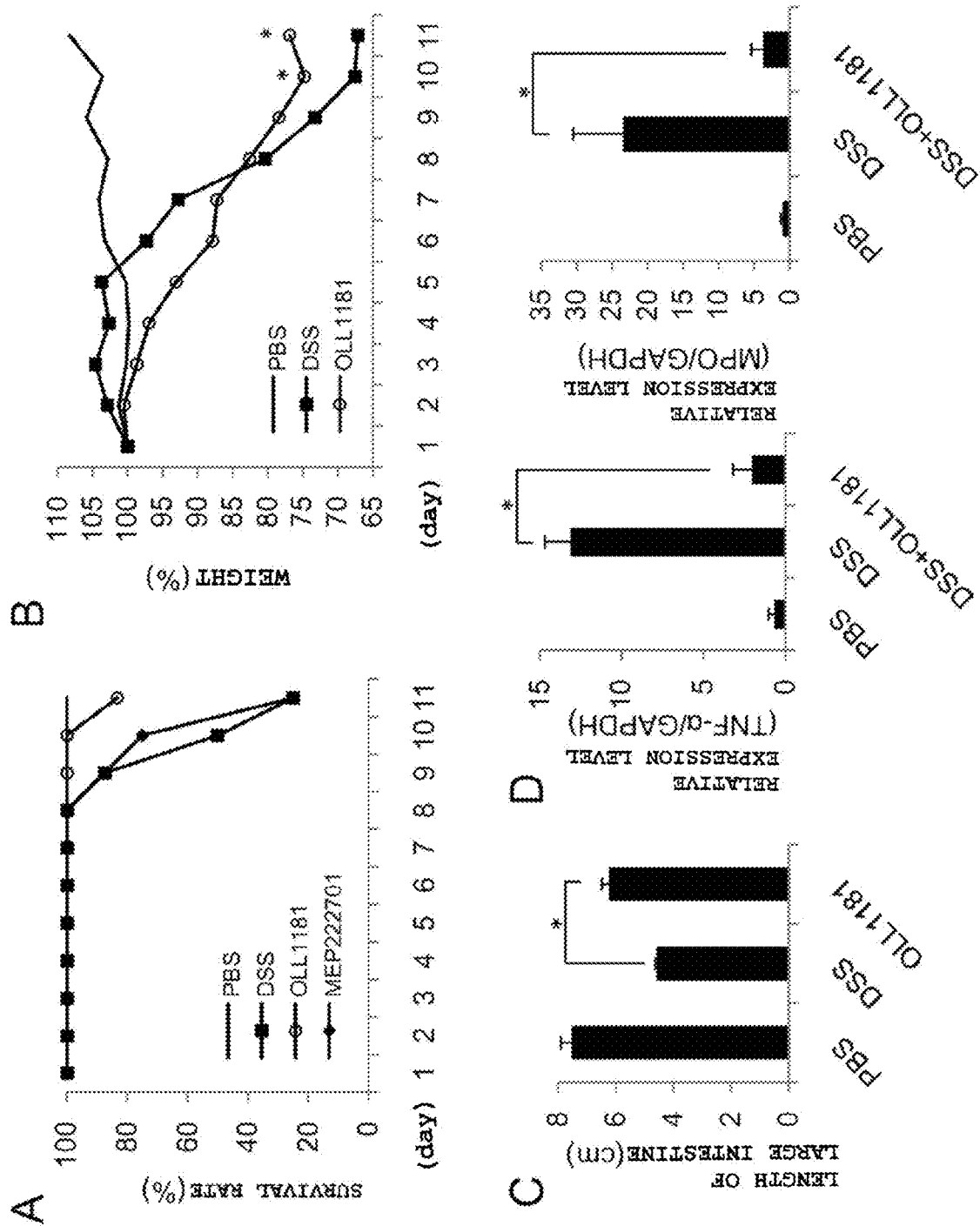
FIG. 6 shows the result of an experiment assessing the effect of OLL1181 strain, which is the strain of the present invention, on DSS-induced enteritis. In each, A: survival rate of each test group, B: change in body weight of each test group, C: length of the large intestine of each test group on $11^{th}$ day, and D: relative amounts of TNF-α and MPO expressed in the large intestine of each test group on $11^{th}$ day.

The results are shown in FIG. 6. A is a graph showing the survival rate of each group up to the $11^{th}$ day. Among groups in which colitis was induced by DSS, in the PBS-administered control group (DSS) and the MEP222701 strain-administered group (MEP222701), the survival rate on the $11^{th}$ day was on the order of 20%, but in the MEP222761 strain-administered group (MEP222761) the survival rate was about 40% (data not shown), and in the OLL1181 strain-administered group (OLL1181) the survival rate was about 80%. In the non-colitis-induced group (PBS) not having DSS administered but having PBS administered none of the mice died.

B shows the change in body weight of the DSS colitis induced group (DSS), the DSS non-colitis-induced group (PBS), and the DSS colitis induced+OLL1181 strain-administered group (OLL1181). In the DSS colitis induced group (DSS), the body weight tended to decrease, but in the OLL1181 strain-administered group, the average body weight exceeded that of the colitis induced group (DSS) on the $8^{th}$ day, and a slight body weight increase was confirmed on the $10^{th}$ day and thereafter.

C shows the length of the large intestine of the DSS colitis induced group (DSS), the DSS non-colitis-induced group (PBS), and the DSS colitis induced+OLL1181 strain-administered group (OLL1181) on the $11^{th}$ day. Compared with the DSS colitis induced group (DSS), the large intestine of the OLL1181 strain-administered group was significantly longer.

D shows the amounts of TNF-α and MPO expressed in the large intestine of the DSS colitis induced group (DSS), the DSS non-colitis-induced group (PBS), and the DSS colitis induced+OLL1181 strain-administered group (DSS+ OLL1181) on the $11^{th}$ day. It is known that TNF-α expression is suppressed by PGE2, and MPO is known as an inflammation marker. In both cases, expression was significantly suppressed in the OLL1181 strain-administered group (DSS+ OLL1181) compared with the DSS colitis induced group (DSS).

Example 7

Production of Cultured Milk Product (Plain Yogurt)

A yogurt base mix was prepared by mixing cow's milk, a dairy product, and water so that the final product had a non-fat solids content of 9.5% and a fat solids content of 3.0%. Subsequently, the yogurt base mix thus prepared was homogenized, then heat-sterilized at 95° C. for 5 minutes, and then cooled to about 40° C.

The yogurt base mix above was inoculated with a mixed starter of *Lactobacillus bulgaricus* (*Lactobacillus bulgaricus* OLL2038) and *Streptococcus thermophilus* (*Streptococcus thermophilus* OLL1131) isolated from 'Meiji Bulgaria Yogurt' and fermented to thus produce a yogurt (control product A). Furthermore, a yogurt (invention product A) was produced by the same method as for the control product except that *Lactobacillus bulgaricus* OLL1181 strain was used instead of *Lactobacillus bulgaricus* OLL2038 of the mixed starter.

From the results of measuring the physical property values as described below, it was shown that the yogurt obtained by production using the OLL1181 strain (invention product A) had a desirable flavor and physical properties at the same level as or better than the control product yogurt (control product A).

TABLE 2

|  | Control product A | Invention product A |
|---|---|---|
| pH | 4.34 | 4.39 |
| Lactic acidity | 0.82 w/w % | 0.81 w/w % |
| Curd tension | 39.9 g | 36.4 g |
| Flavor | Good | Good |

Example 8

Production of Cultured Milk Product (Drinking Yogurt)

A drinking yogurt base mix was prepared by mixing cow's milk, a dairy product, and water so that the final product had a non-fat solids content of 8.0% and a fat solids content of 0.5%, it was homogenized, then heat-sterilized at 95° C. for 10 minutes, and then cooled to about 40° C. This drinking yogurt base mix above was inoculated with the same yogurt starter as that of Example 8 (a mixed starter of *Lactobacillus bulgaricus* (*Lactobacillus bulgaricus* OLL2038) and *Streptococcus thermophilus* (*Streptococcus thermophilus* OLL1131) isolated from 'Meiji Bulgaria Yogurt') and fermented to thus prepare cultured milk for drinking yogurt. The cultured milk for drinking yogurt thus obtained was homogenized, thus giving liquid cultured milk for drinking yogurt. This liquid cultured milk for drinking yogurt and a sterilized sugar solution were mixed at a ratio by mass of 6:4, thus producing a drinking yogurt (control product B). Furthermore, a drinking yogurt (invention product B) was produced by the same method as for the control product except that

*Lactobacillus bulgaricus* OLL1181 strain was used instead of the *Lactobacillus bulgaricus* OLL2038 of the mixed starter.

From the result of measuring the physical property values as described below, it was shown that the drinking yogurt obtained by production using the OLL1181 strain (invention product B) had a desirable flavor and physical properties at the same level as or better than the control drinking yogurt (control product B).

TABLE 3

|  | Control product B | Invention product B |
| --- | --- | --- |
| pH | 4.17 | 4.15 |
| Lactic acidity | 0.79 w/w % | 0.79 w/w % |
| Viscosity | 23.5 mPa · s | 23.2 mPa · s |
| Flavor | Good | Good |

Measurement Methods for Physical Properties

Measurement of pH was carried out using a glass electrode pH meter (HM30-R, manufactured by DKK-TOA) at 5° C.

Lactic acidity was titrated using 0.1 N NaOH with phenolphthalein as an indicator, and calculated.

With regard to the curd tension of a yogurt, constant rate loading was imposed on a sample via a spring using a MAX ME500 curdmeter (Asuka Kiki) with a weight of 100 g, the strain caused by deformation was measured using a load cell, and the elasticity at break was defined as the hardness (g).

The viscosity was measured at a product temperature of 5° C. using an RB200 model RC-100 controller (Toki Sangyo Co., Ltd.) with a No. 1 rotor under conditions of 60 rpm and 30 seconds.

Flavor was assessed by five specialist panelists using three categories of good, fair, and poor.

INDUSTRIAL APPLICABILITY

In accordance with the probiotic(s) of the present invention, an inflammatory gastrointestinal tract disease can be alleviated by action on the enteric environment, and it becomes possible to completely treat an inflammatory gastrointestinal tract disease that has hitherto been intractable and has only been subjected to symptomatic therapy with a medicinal agent. Furthermore, since the probiotic(s) of the present invention does not have biological toxicity, it can be taken simply and effectively by adding it to a pharmaceutical composition or a food composition.

The invention claimed is:

1. A cultured milk product produced by using a probiotic having aryl hydrocarbon receptor (AhR) activating potency.

2. The cultured milk product according to claim 1, wherein the probiotic is selected from the group consisting of a Lactic acid bacterium, a *Bifidobacterium*, and a Propionic acid bacterium.

3. The cultured milk product according to claim 1, wherein the isolated probiotic is an isolated Lactic acid bacterium.

4. The cultured milk product according to claim 1, wherein the probiotic is *Lactobacillus delbrueckii* subsp. *bulgaricus* OLL1181 strain (depository number: FERM BP-11269).

5. A cultured milk product comprising an anti-inflammatory agent comprising a probiotic having aryl hydrocarbon receptor (AhR) activating potency.

6. The cultured milk product according to claim 5, wherein the probiotic having AhR-activating potency is selected from the group consisting of a Lactic acid bacterium, a *Bifidobacterium*, and a Propionic acid bacterium.

7. The cultured milk product according to claim 5, wherein the probiotic having AhR-activating potency is a Lactic acid bacterium.

8. The cultured milk product according to claim 5, wherein the probiotic having AhR-activating potency is *Lactobacillus delbrueckii* subsp. *bulgaricus* OLL1181 strain (depository number: FERM BP-11269).

* * * * *